(12) United States Patent
Vitullo et al.

(10) Patent No.: US 6,896,671 B2
(45) Date of Patent: May 24, 2005

(54) CATHETER WITH LIMITED LONGITUDINAL EXTENSION

(75) Inventors: Jeffrey M. Vitullo, Pottstown, PA (US); Richard Harding, Reinholds, PA (US)

(73) Assignee: Arrow International, Inc., Reading, PA (US)

( * ) Notice: Subject to any disclaimer, the term of this patent is extended or adjusted under 35 U.S.C. 154(b) by 170 days.

(21) Appl. No.: 10/387,300

(22) Filed: Mar. 12, 2003

(65) Prior Publication Data

US 2004/0181207 A1 Sep. 16, 2004

(51) Int. Cl.[7] .............................................. A61M 25/00
(52) U.S. Cl. ...................................... 604/526; 604/524
(58) Field of Search ................................. 604/523–528

(56) References Cited

U.S. PATENT DOCUMENTS

| | | | | | |
|---|---|---|---|---|---|
| 2,268,321 | A | * | 12/1941 | Flynn | 138/118 |
| 3,498,286 | A | * | 3/1970 | Polanyi et al. | 600/325 |
| 4,447,239 | A | * | 5/1984 | Krutten | 604/529 |
| 5,057,092 | A | * | 10/1991 | Webster, Jr. | 604/527 |
| 5,176,660 | A | * | 1/1993 | Truckai | 604/527 |
| 5,251,640 | A | * | 10/1993 | Osborne | 600/585 |
| 5,827,242 | A | * | 10/1998 | Follmer et al. | 604/526 |
| 6,022,343 | A | * | 2/2000 | Johnson et al. | 604/526 |
| 6,090,099 | A | * | 7/2000 | Samson et al. | 604/527 |
| 6,290,692 | B1 | * | 9/2001 | Klima et al. | 604/524 |
| 2003/0191451 | A1 | * | 10/2003 | Gilmartin | 604/527 |
| 2004/0181208 | A1 | * | 9/2004 | Poole | 604/527 |

OTHER PUBLICATIONS

Arrow Epidural Products, 2001.
"Arrow Epidural Products" brochure, 2001 and 4 internal blueprints, 2001 of two products described therein.

* cited by examiner

*Primary Examiner*—Sharon Kennedy
(74) *Attorney, Agent, or Firm*—Amster, Rothstein & Ebenstein (57) ABSTRACT

A catheter includes a tube formed of plastic, a helical spring coil formed of metal and a ribbon which is longitudinally substantially non-extendable. The coil is coaxially disposed within the tube and substantially coextensive longitudinally with the tube. The ribbon is disposed within the coil, proximal ends of the ribbon and the coil being secured together, and the ribbon distal end being secured to the coil body at a predetermined point of the coil body adjacent but substantially proximally spaced from the coil distal end. The ribbon precludes substantial longitudinal extension of the coil body intermediate the coil proximal end and the predetermined point, thereby to limit longitudinal extension and increase the pull strength of the catheter.

15 Claims, 6 Drawing Sheets

CATHETER WITH LIMITED LONGITUDINAL EXTENSION

BACKGROUND OF THE INVENTION

The present invention relates to a catheter such as an epidural catheter, and more particularly to such a catheter characterized by a limited longitudinal extension and increased pull strength.

In its basic form, a catheter is essentially a flexible tube formed of plastic defining a tube proximal end, a tube distal end, and a tube body connecting the tube proximal and distal ends such that liquid entering one tube end passes through the tube body and exits through the other tube end. Improved catheters frequently have a helical spring coil formed of metal defining a coil proximal end, a coil distal end, and a coil connecting the coil proximal and distal ends. The coil is coaxially disposed within the tube for the purpose of limiting, and hopefully precluding, kinking of the tube during its insertion into and passage through a patient's body. The tube and coil are separately formed, but are typically substantially coextensive longitudinally. During assembly the tube is expanded radially in inner diameter (for example, through the use of a solvent), the coil is then inserted into the tube, and the tube is then allowed to return to its original dimensions (for example, through solvent evaporation) such that it snugly hugs the coil.

A particularly useful embodiment of such a catheter (especially for an epidural catheter) uses a coil which is axially or longitudinally expanded at or adjacent the coil distal end so that the tip or distal end of the catheter is softer and more flexible than the proximal remainder of the catheter. The soft, flexible tip of such a catheter embodiment enables it to more closely and safely follow an intended tortuous path through the body passageways (e.g., veins).

When it comes time for the removal of a catheter from the patient, the pull force exerted on the catheter by the medical personnel typically results in an elongation or longitudinal extension of the catheter (both within and without the patient's body) as neither the plastic tube nor the metal coil exhibits any high resistance to elongation (that is, any high pull strength). For example, a nineteen gauge catheter with a length of 35½ inches may exhibit an elongation of about 15 inches in response to a pull force of 8 pounds. Such a high elongation and low pull strength is undesirable since it increases both the energy and time required for medical personnel (e.g., a surgeon) to remove the catheter from the patient.

Accordingly, it is an object of the present invention to provide a catheter which exhibits a limited longitudinal extension and high pull strength.

Another object is to provide such a catheter which in one preferred embodiment can be more easily and rapidly removed from a patient than a conventional catheter.

A further object is to provide such a catheter which in one preferred embodiment is a nineteen gauge catheter which exhibits an elongation of less than 4 inches at a force of 11 pounds.

It is also an object of the present invention to provide such a catheter which is simple and economical to manufacture, use, and maintain.

SUMMARY OF THE INVENTION

It has now been found that the above and related objects of the present invention are obtained in a catheter comprising a tube, a helical spring coil, and a ribbon. The tube is formed of plastic and defines a tube proximal end, a tube distal end, and a tube body connecting the tube proximal and distal ends. The helical spring coil is formed of metal and defines a coil proximal end, a coil distal end, and a coil body connecting the coil proximal and distal ends. The ribbon is longitudinally substantially non-extendable and defines a ribbon proximal end, a ribbon distal end, and a ribbon body connecting the ribbon proximal and distal ends.

In the first embodiment the coil is coaxially disposed within the tube and is substantially coextensive longitudinally with the tube. The ribbon is disposed within the coil, the proximal ends of the ribbon and the coil being secured together, and the ribbon distal end being secured to the coil body at a predetermined point on the coil body adjacent but substantially proximally spaced from the coil distal end. Thus, the ribbon precludes substantial longitudinal extension of the coil body intermediate the coil proximal end and the predetermined point of the coil body, thereby to limit longitudinal extension and increase the pull strength of the catheter.

Preferably the coil body in turn defines a coil tip connecting the predetermined point and the coil distal end, and a coil corpus connecting the predetermined point and the coil proximal end, the coil tip extending less than 3 inches and being substantially more soft and more flexible than the coil corpus. The tube and the coil are generally cylindrical and hollow, the proximal ends and the distal ends of the tube and the coil being open for liquid communication therebetween and therethrough. The ribbon is of generally rectangular cross section and formed of metal. The proximal ends of the ribbon and the coil are secured together by welding, and the distal end of the ribbon and the predetermined point of the coil body are secured by welding.

The catheter is preferably an epidural catheter. The coil may include at least one extended coil portion for use as a flashback window intermediate the coil proximal end and the predetermined point.

In a variant of the first embodiment, the ribbon body and the coil body are secured together at at least one point intermediate the proximal ends of the ribbon and the coil and the predetermined point, thereby to enable trimming of the proximal longitudinal length of the catheter. Preferably the ribbon body and the coil body are secured together at a plurality of longitudinally spaced points intermediate the coil proximal end and the predetermined point, thereby to enable selective trimming of the proximal longitudinal length of the catheter adjacent any of such points.

In the second embodiment, the coil is coaxially disposed within the tube and substantially coextensive longitudinally with the tube. The ribbon is disposed within the coil, the proximal ends of the ribbon and the coil being secured together, and the distal ends of the ribbon and the coil being secured together. Thus, the ribbon precludes substantial longitudinal extension of the coil, thereby to limit longitudinal extension and increase the pull strength of the catheter.

In the third embodiment, the coil is coaxially disposed within the tube and extends distally to a predetermined point of the tube body adjacent but substantially proximally spaced from the tube distal end. The ribbon is disposed within the coil and is substantially coextensive longitudinally with the coil, the proximal ends of the ribbon and the coil being secured together, and the distal ends of the ribbon and the coil being secured together. Thus, the ribbon precludes substantial longitudinal extension of the coil, thereby to limit longitudinal extension and increase the pull strength of the catheter.

In all embodiments the ribbon is less extendable longitudinally than the coil.

BRIEF DESCRIPTION OF THE DRAWING

The above and related objects, features and advantages of the present invention will be more fully understood by reference to the following detailed description of the presently preferred, albeit illustrative, embodiments of the present invention when taken in conjunction with the accompanying drawing wherein.

Structurally and/or functionally similar elements in the various embodiments are designated by the same reference numeral.

DETAILED DESCRIPTION OF THE PREFERRED EMBODIMENTS

Referring now to the drawing, and in particular to FIGS. 1–4 thereof, therein illustrated is a first embodiment of a catheter according to the present invention, generally designated by the reference numeral 10.

Basically, the catheter 10 comprises a tube generally designated 12, a coil generally designated 14, and a ribbon generally designated 16. More particularly, the tube 12 defines a tube proximal end 12a, a tube distal end 12b, and a tube body 12c connecting the tube proximal and distal ends 12a, 12b. The helical spring coil defines a coil proximal end 14a, a coil distal end 14b, and a coil body 14c connecting the coil proximal and distal ends 14a, 14b. The ribbon 16 is longitudinally substantially non-extendable and defines a ribbon proximal end 16a, a ribbon distal end 16b, and a ribbon body 16c connecting the ribbon proximal and distal ends 16a, 16b.

The single lumen tube 12 is longitudinally extendable and preferably formed of a surgically acceptable soft flexible plastic, such as polyurethane, or a like material. It is preferably transparent (although it may be opaque). By way of example, the catheter may be nineteen gauge. Preferably the outer surface of the tube body 12c contains longitudinally spaced, circumferentially extending markings 18 formed of non-toxic ink indicating particular longitudinal lengths of the tube body 12c from the tube distal end 12b. The markings 18 may be radio-opaque to facilitate viewing thereof when they are disposed within the patient's body.

The coaxial coil 14 is longitudinally extendable and is preferably formed of a metal, such as a surgically acceptable stainless steel, or like material. An especially preferred metal is a kink-resistant alloy comprising 304V stainless steel or XM-19 high alloy steel, both available from Fort Wayne Metals, Inc. of Indiana. By way of example, a spring coil 0.0285 inches in outer diameter may be used with a nineteen gauge tube 12. The coil turns are preferably of a uniform pitch throughout the coil body 14c, except for a distal portion 14b disposed in the tip of the catheter and, possibly, as required for flashback windows (used to detect the presence of blood in the catheter interior). The coil pitch in coil distal portion 14b is substantially less than the remainder of coil body 14c so that the coil distal portion 14b and the surrounding tube distal portion 12d together define a soft, flexible distal tip (that is a relatively soft, relatively flexible portion) of the catheter 10. Accordingly, it is appropriate to consider the catheter 10 as being composed of a relatively hard, relatively inflexible corpus 10a and a relatively soft, relatively flexible tip 10b, typically about 3 inches in length.

The length of the catheter 10 will vary with its intended use, a length of 35½ inches being exemplary. Preferably the tube 12 is slightly longer than the coil 14 so that the tube distal end 12b slightly covers the coil distal end 14b and the tube proximal end 12b slightly covers the coil proximal end 14a, thereby ensuring that the coil 14 is not exposed at the ends of the catheter 10.

The tube 12 and coil 14 are generally cylindrical and hollow, with the proximal and distal ends thereof preferably being open so that there is liquid communication between and through the tube ends 12a, 12b-in other words, catheter discharge is preferably through an end hole rather than a side hole.

The ribbon 16 is disposed within the coil 14, although typically not coaxially therewith. The ribbon proximal end 16a and the coil proximal end 14a are secured together at 19, for example, by spot or other resistance welding. The ribbon distal end 16b is secured to the coil body 14c at a predetermined point 20 of the coil body 14c. This predetermined point 20 is adjacent, but substantially proximally spaced from, the coil distal end 14b. Preferably the predetermined point 20 is disposed at the junction of the catheter corpus 10a and the catheter tip 10b. The ribbon distal end 16b and coil body 14c may be joined together by the same or a different technique than the proximal ends 14a, 16a of the coil and ribbon-e.g., by spot or other resistance welding, or other means for securing two metal pieces together.

The ribbon 16 is longitudinally substantially non-extendable and preferably formed of a metal, such as a surgically acceptable stainless steel, or like material. For example, the ribbon 16 may be made of the same material as coil 14, but it is less extendable longitudinally than the coil 14 (or tube 12) due to its configuration and dimensions. The ribbon 16 is typically of a rectangular cross section to enable flexing of the ribbon along at least one axis. Preferred dimensions for the cross section of the ribbon 16 are 0.003×0.010 inches.

Because the ribbon 16 is longitudinally substantially non-extendable, it precludes any substantial longitudinal extension of the coil body 14c intermediate the coil proximal end 14a and the predetermined point 20 of the coil body 14c. The ribbon 16 thereby limits longitudinal extension of the catheter 10 to the catheter tip 10b, thereby limiting longitudinal extension of the entire catheter and increasing the pull strength of the entire catheter.

In a preferred embodiment, the tube body 12c is transparent and the coil 14 includes one or more short portions of lesser pitch intermediate the coil proximal end 14a and the predetermined point 20 for use as flashback windows.

Figure 5:
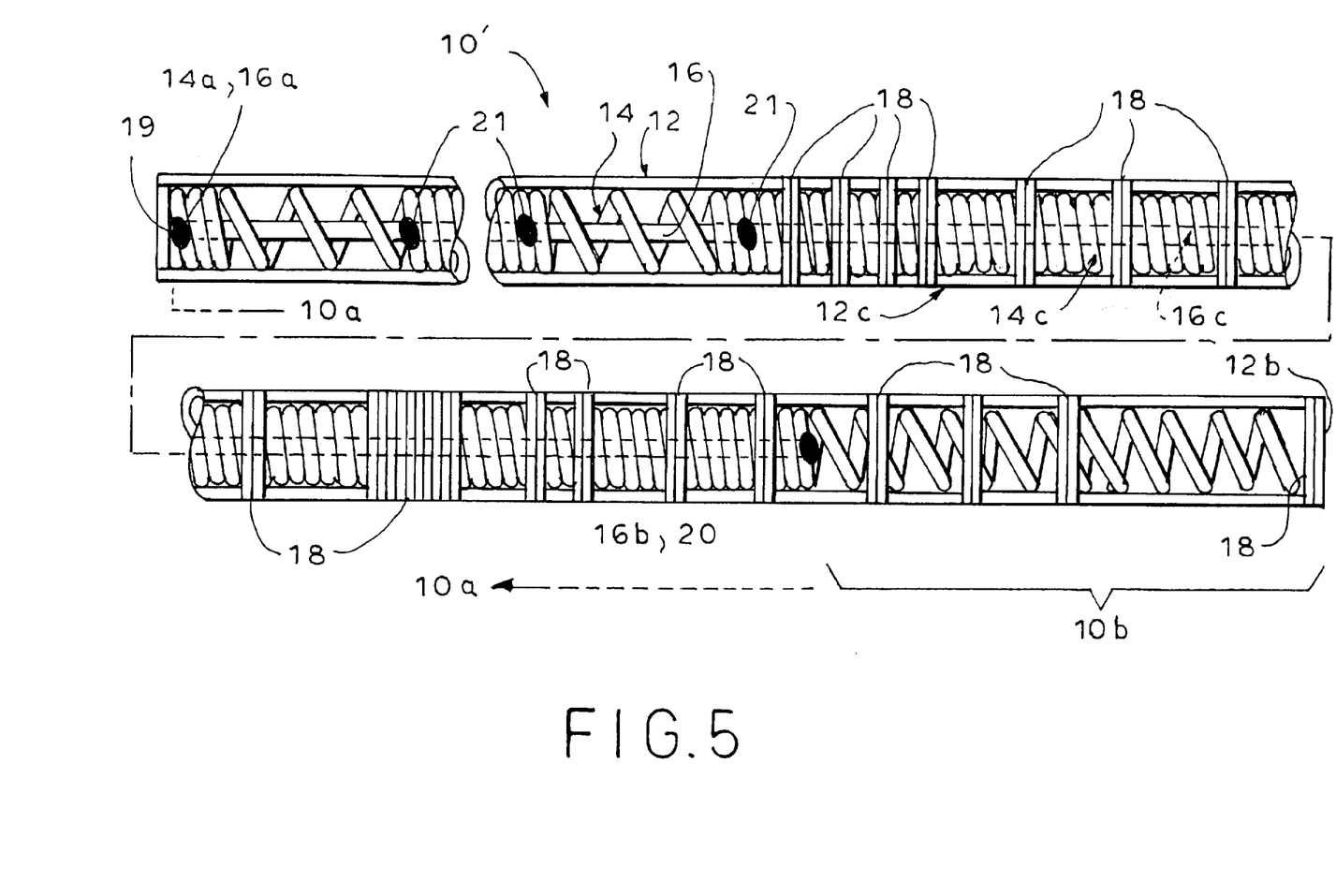
FIG. 5 is a view, similar to FIG. 1, of a variant of the first embodiment enabling proximal trimming of the catheter length.

Referring now to FIG. 5, in order to allow the catheter to be trimmed to an appropriate length without loss or diminution of the soft, flexible catheter tip 10b, in a variant 10' of the first embodiment the ribbon body 16c and the coil body 14c are secured together at at least one point 21 intermediate the coil proximal end 14a and said predetermined point 20, thereby to enable trimming of the proximal longitudinal length of the catheter 10 (that is, trimming from the proximal end). Preferably, they are secured together at a longitudinally spaced plurality of such points 21 (three being illustrated) to enable selective trimming proximally of any one of such points 21.

Figure 6:
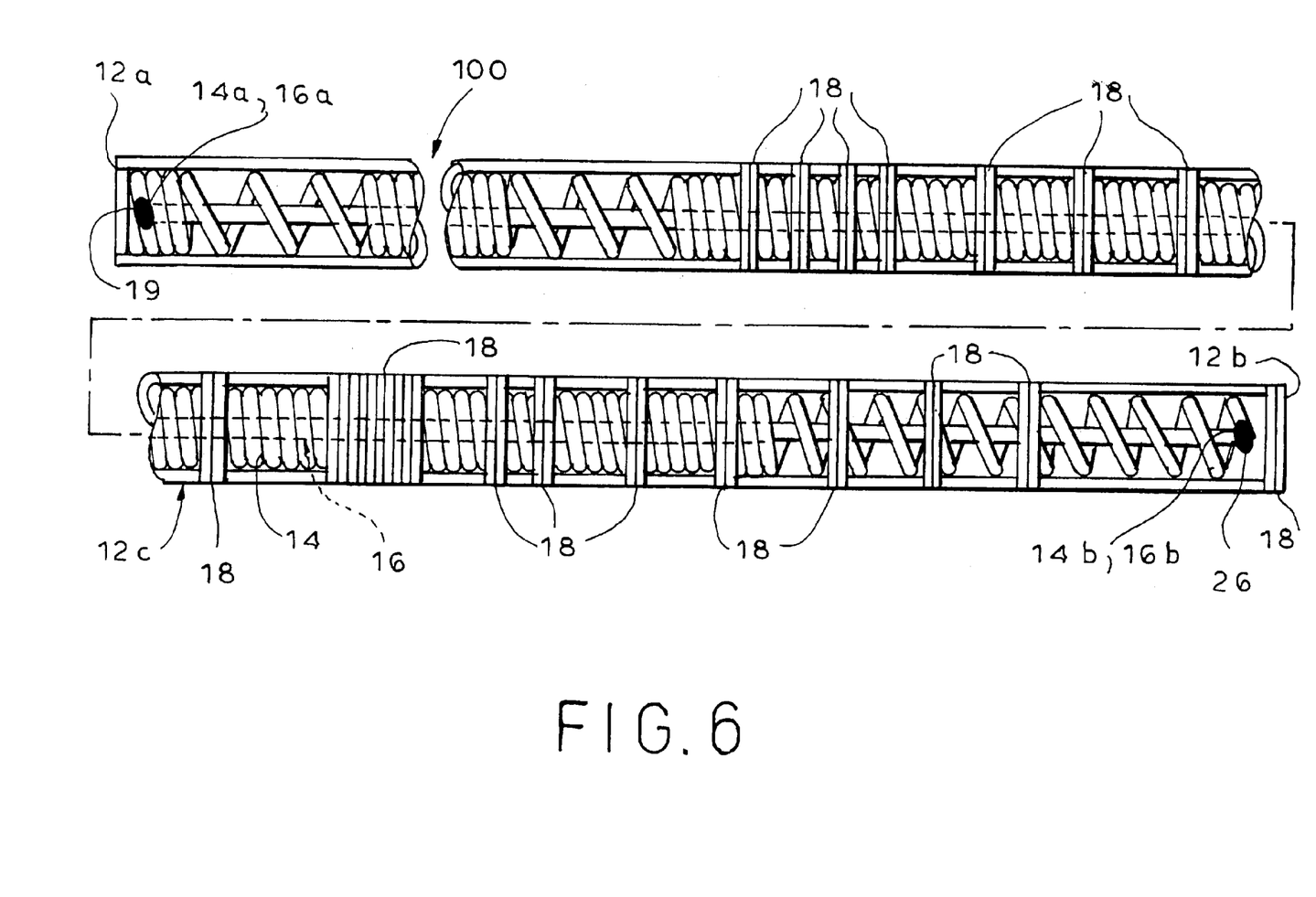
FIG. 6 is a view, similar to FIG. 1, of a second embodiment of the present invention.

Referring now to FIG. 6, therein illustrated is a second embodiment 100 of the present invention which precludes substantial longitudinal extension of the coil 14, thereby to preclude longitudinal extension and increase the pull strength of the catheter 100. In this embodiment the ribbon 16 and coil 14 are substantially longitudinally coextensive and secured together both at the proximal ends 16a, 14a thereof (at 19) and at the distal ends 16b, 14b thereof (at 26). Thus the ribbon 16 precludes substantial longitudinal extension of any portion of the coil 14, thereby to not only limit, but preclude, substantial longitudinal extension of the catheter 10 in its entirety. On the other hand, in the second embodiment 100 the presence of the ribbon 16 within the catheter tip 10b somewhat reduces the softness and flexibility thereof.

Figure 7:
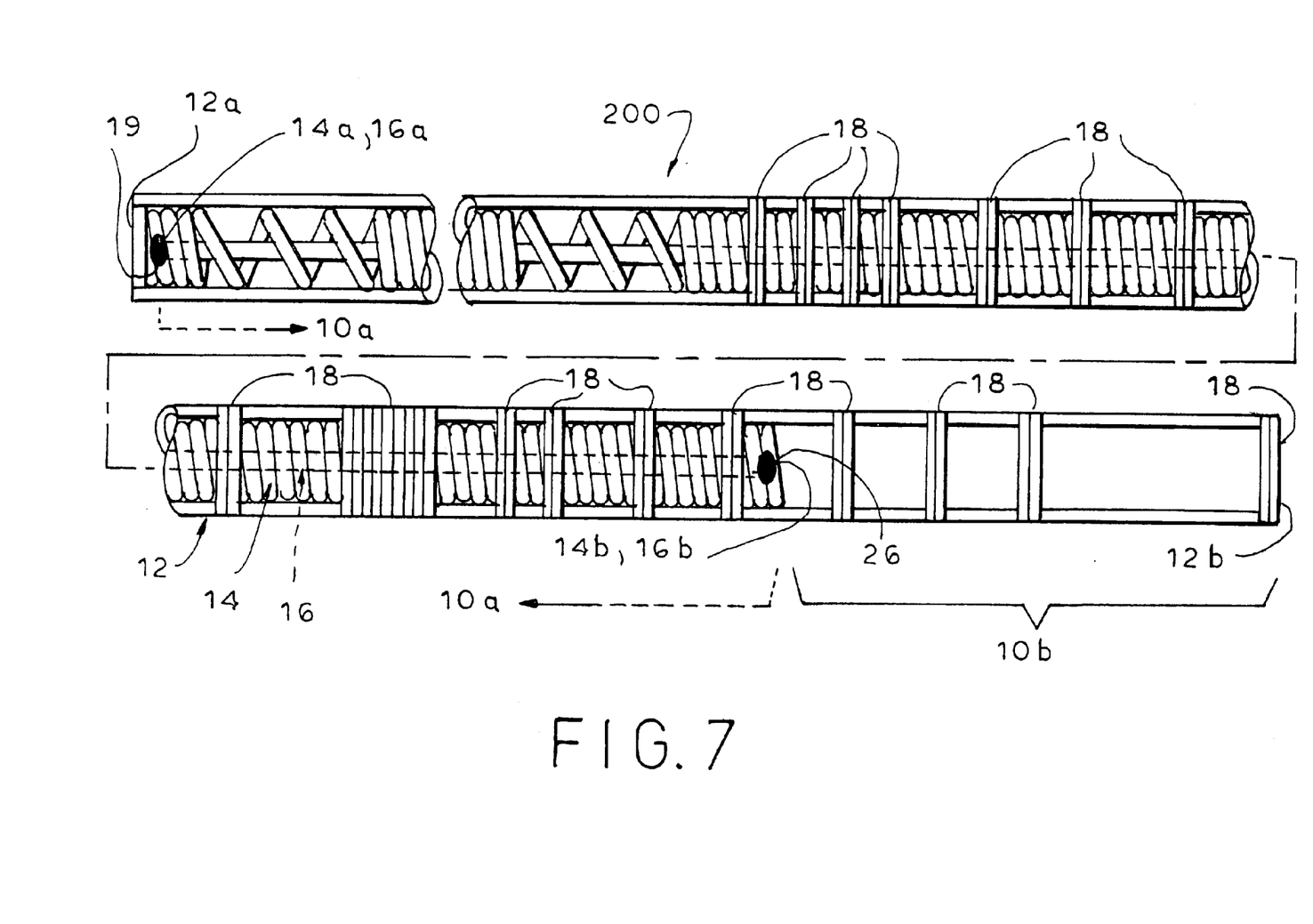
FIG. 7 is a view, similar to FIG. 1, of a third embodiment of the present invention.

Referring now to FIG. 7, therein illustrated is a third embodiment 200 of the present invention wherein the catheter tip 10b is of maximum softness and flexibility. In this embodiment the coil 14 is not substantially coextensive longitudinally with the tube, but rather extends distally only to a predetermined point 26 of the tube body 12c adjacent, but substantially proximally spaced from, the tube distal end 12b. As in the second embodiment 100, the ribbon 16 and coil 14 are substantially longitudinally coextensive. The ribbon proximal end 16a and the coil proximal end 14a are secured together at 19, and the ribbon distal end 16b and the coil distal end 14b are secured together at 26. Thus, the ribbon 16 precludes substantial longitudinal extension of the coil 14, thereby limiting longitudinal extension of the catheter 200 to the portion of the tube 12 distally beyond the predetermined point 26-i.e., the tube portion forming the catheter tip 10b. Accordingly, the ribbon 16 limits longitudinal extension and increases the pull strength of the catheter 200.

Figure 1:
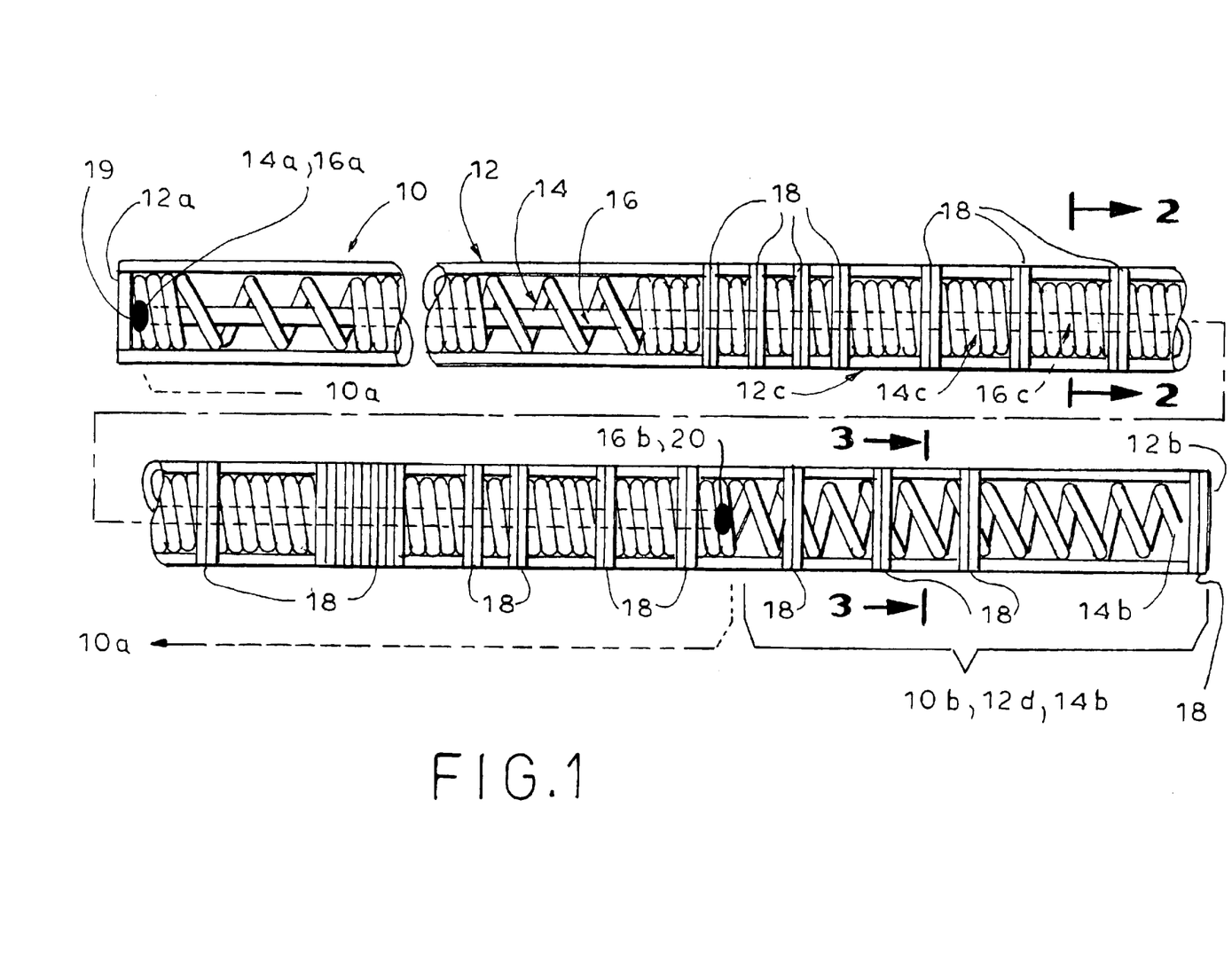
FIG. 1 is a side elevational view of a first embodiment of a catheter according to the present invention; with a portion of the tube removed to reveal details of internal construction.
Figure 2:
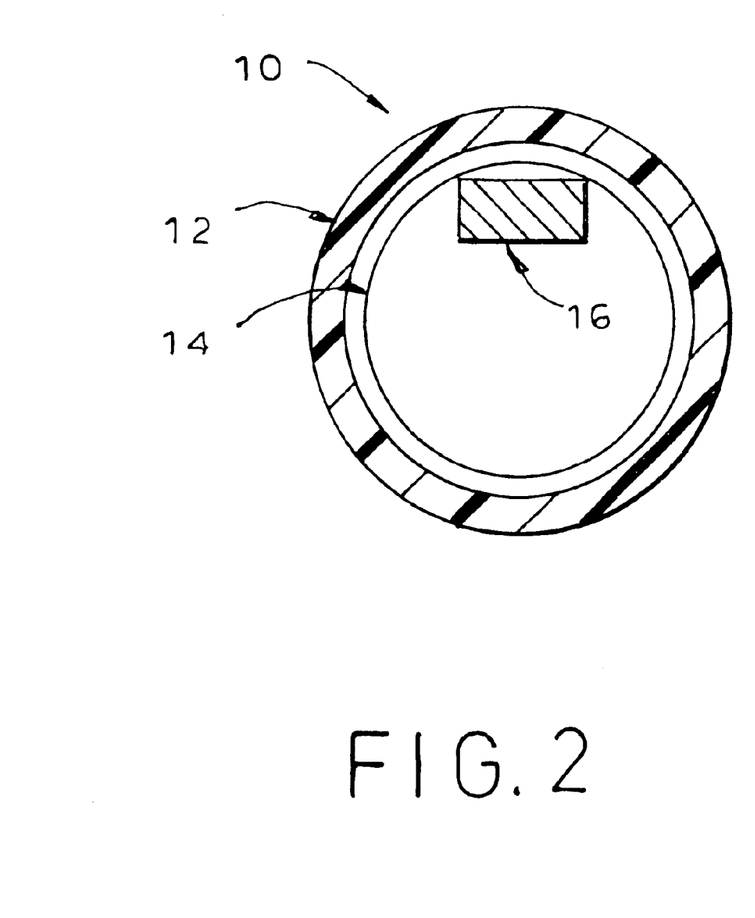
FIG. 2 is a sectional view thereof taken along the line 2—2 of FIG. 1.
Figure 3:
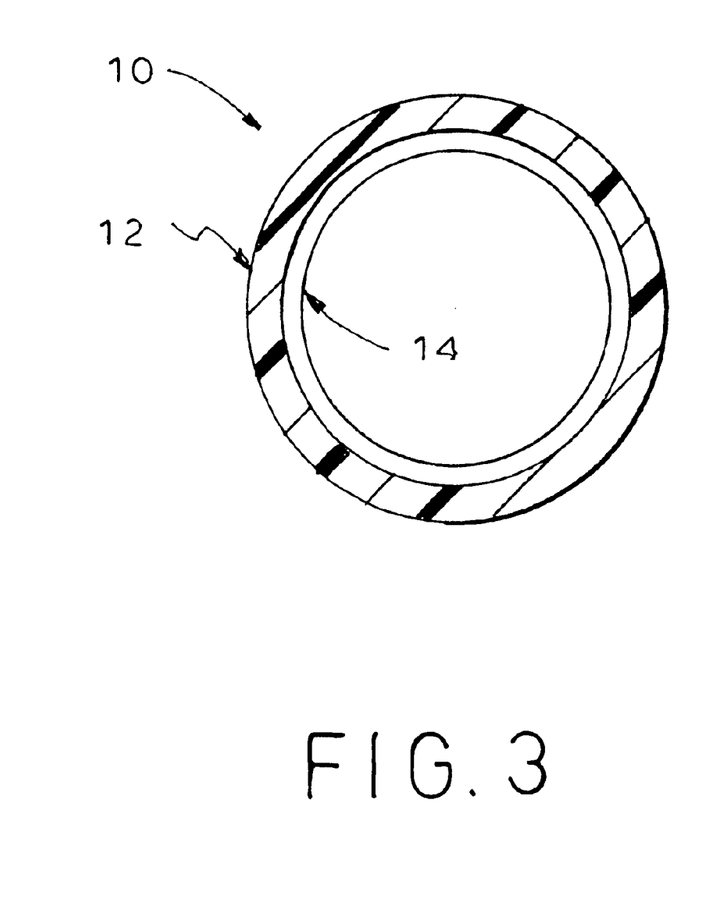
FIG. 3 is a sectional view thereof taken along the line 3—3 of FIG. 1.
Figure 4:
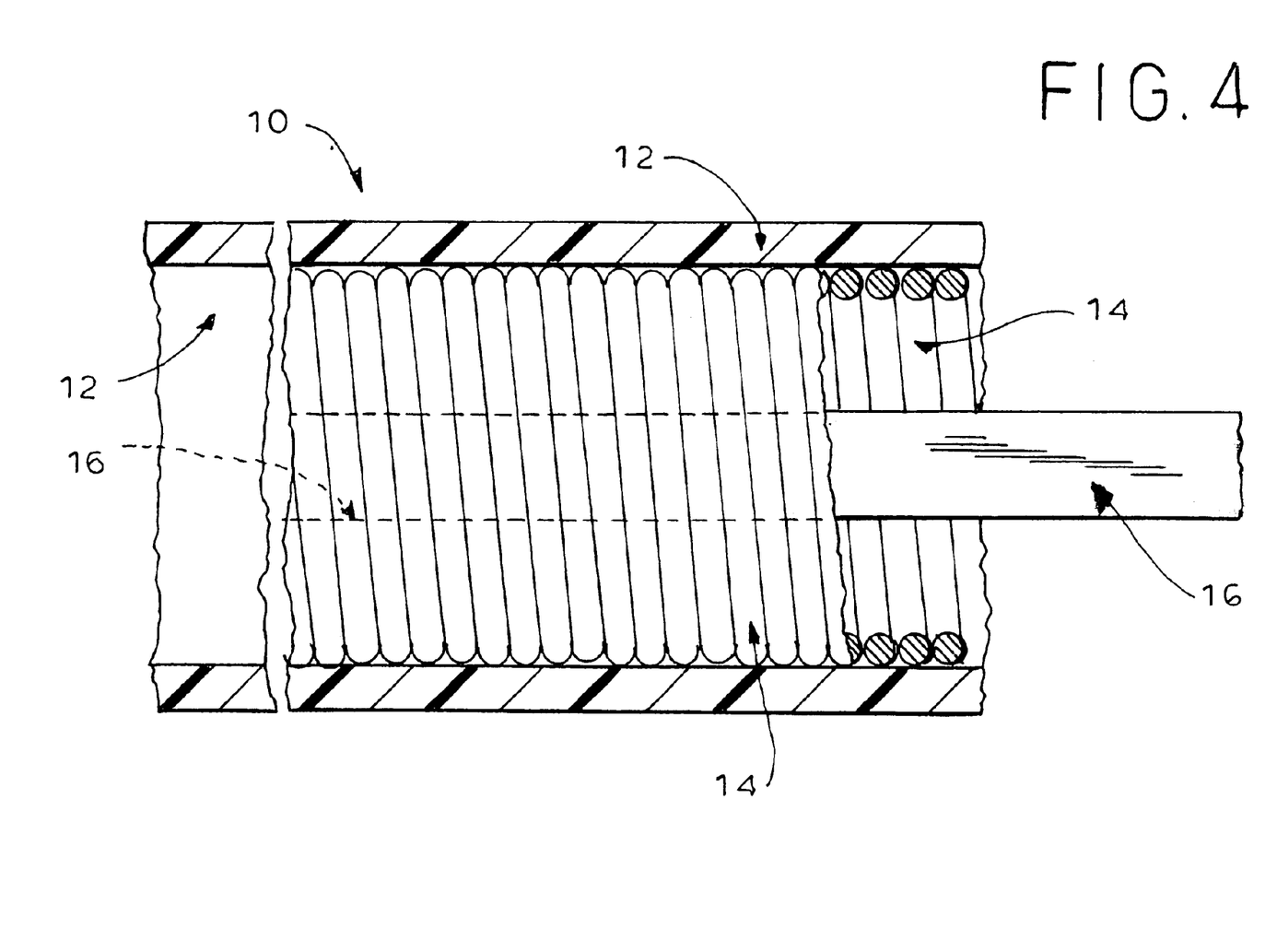
FIG. 4 is a sectional view of a longitudinal segment thereof, with portions successively cut away to reveal details of internal construction.

Thus, in the first embodiment 10, the coil 14 and tube 12 are substantially coextensive longitudinally, but the ribbon distal end 16b is substantially proximally spaced from the coil distal end 14b. In the second embodiment 100, the coil 14, tube 12 and ribbon 16 are substantially coextensive longitudinally. In the third embodiment 200, the ribbon 16 and coil 14 are substantially coextensive longitudinally, but the coil distal end 14b is substantially proximally spaced from the tube distal end 12b.

To summarize further, the present invention provides a catheter which exhibits a limited longitudinal extension and high pull strength such that it can be more easily and rapidly removed from the patient than a conventional catheter. For example, a nineteen gauge catheter exhibits an elongation of less than 4 inches in response to a pull force of 11 pounds. The catheter is simple and economical to manufacture, use and maintain.

Now that the preferred embodiments of the present invention have been shown and described in detail, various modifications and improvements thereon will become readily apparent to those skilled in the art. Accordingly, the spirit and scope of the present invention is to be limited only by the appended claims, and not by the foregoing specification.

We claim:

1. A catheter comprising:
   (A) a tube formed of plastic defining a tube proximal end, a tube distal end, and a tube body connecting said tube proximal and distal ends;
   (B) a helical spring coil formed of metal defining a coil proximal end, a coil distal end, and a coil body connecting said coil proximal and distal ends; and
   (C) a ribbon which is longitudinally substantially non-extendable and defines a ribbon proximal end, a ribbon distal end, and a ribbon body connecting said ribbon proximal and distal ends;
   said coil being coaxially disposed within said tube and substantially coextensive longitudinally with said tube;
   said ribbon being disposed within said coil, said proximal ends of said ribbon and said coil being secured together, and said ribbon distal end being secured to said coil body at a predetermined point on said coil body adjacent but proximally spaced from said coil distal end;
   whereby said ribbon precludes substantial longitudinal extension of said coil body intermediate said coil proximal end and said predetermined point on said coil body, thereby to limit longitudinal extension and increase the pull strength of said catheter.

2. The catheter of claim 1 wherein said coil body in turn defines a coil tip connecting said predetermined point and said coil distal end, and a coil corpus connecting said predetermined point and said coil proximal end;
   said coil tip extending less than 3 inches and being substantially more soft and more flexible than said coil corpus.

3. The catheter of claim 1 wherein said tube and said coil are generally cylindrical and hollow.

4. The catheter of claim 3 wherein said proximal ends and said distal ends of said tube and said coil are open for liquid communication therebetween and therethrough.

5. The catheter of claim 1 wherein said ribbon is of generally rectangular cross section.

6. The catheter of claim 1 wherein said ribbon is formed of metal.

7. The catheter of claim 1 wherein said coil includes at least one extended coil portion for use as a flashback window intermediate said coil proximal end and said predetermined point.

8. The catheter of claim 1 wherein said catheter is an epidural catheter.

9. The catheter of claim 1 wherein said proximal ends of said ribbon and said coil are secured together by welding.

10. The catheter of claim 1 where said distal end of said ribbon and said predetermined point of said coil body are secured by welding.

11. The catheter of claim 1 wherein said ribbon body and said coil body are secured together at at least one point intermediate said proximal ends of said ribbon and said coil and said predetermined point, thereby to enable trimming of the proximal longitudinal length of said catheter.

12. The catheter of claim 11 wherein said ribbon body and said coil body are secured together at a plurality of longitudinally spaced points intermediate said coil proximal end and said predetermined point, thereby to enable selective trimming of the proximal longitudinal length of said catheter adjacent any of such points.

13. A catheter comprising:

(A) a tube formed of plastic defining a tube proximal end, a tube distal end, and a tube body connecting said tube proximal and distal ends;

(B) a helical spring coil formed of metal defining a coil proximal end, a coil distal end and a coil body connecting said coil proximal and distal ends; and (C) a ribbon which is longitudinally substantially nonextendable and defines a ribbon proximal end, a ribbon distal end, and a ribbon body connecting said ribbon proximal and distal ends;

said coil being coaxially disposed within said tube and substantially coextensive longitudinally with said tube;

said ribbon being disposed within said coil, said proximal ends of said ribbon and said coil being secured together, and said distal ends of said ribbon and said coil being secured together;

whereby said ribbon precludes substantial longitudinal extension of said coil, thereby to limit longitudinal extension and increase the pull strength of said catheter.

14. A catheter comprising:

(A) a tube formed of plastic defining a tube proximal end, a tube distal end, and a tube body connecting said tube proximal and distal ends;

(B) a helical spring coil formed of metal defining a coil proximal end, a coil distal end and a coil body connecting said coil proximal and distal ends; and (C) a ribbon which is longitudinally substantially nonextendable and defines a ribbon proximal end, a ribbon distal end, and a ribbon body connecting said ribbon proximal and distal ends;

said coil being coaxially disposed within said tube and extending distally to a predetermined point of said tube body adjacent but proximally spaced from said tube distal end;

said ribbon being disposed within said coil and being substantially coextensive longitudinally with said coil, said proximal ends of said ribbon and said coil being secured together, and said distal ends of said ribbon and said coil being secured together;

whereby said ribbon precludes substantial longitudinal extension of said coil, thereby to limit longitudinal extension and increase the pull strength of said catheter.

15. A catheter comprising:

(A) a tube formed of plastic defining a tube proximal end, a tube distal end, and a tube body connecting said tube proximal and distal ends;

(B) a helical spring coil formed of metal defining a coil proximal end, a coil distal end, and a coil body connecting said coil proximal and distal ends; and (C) a ribbon which is longitudinally extendable less than said coil and defines a ribbon proximal end, a ribbon distal end, and a ribbon body connecting said ribbon proximal and distal ends;

said ribbon being disposed within said coil;

said coil being coaxially disposed within said tube;

said proximal ends of said ribbon and said coil being secured together, and said ribbon distal end being secured to said coil body at a predetermined point on said coil body adjacent said coil distal end; and whereby said ribbon limits longitudinal extension of said coil body intermediate said coil proximal end and said predetermined point on said coil body, thereby to limit longitudinal extension and increase the pull strength of said catheter.

* * * * *